United States Patent
Nakamura et al.

(10) Patent No.: US 6,211,293 B1
(45) Date of Patent: *Apr. 3, 2001

(54) POLYCARBODIIMIDE COMPOUND, PRODUCTION PROCESS THEREOF, RESIN COMPOSITION, AND TREATMENT METHOD OF ARTICLE

(75) Inventors: Michiei Nakamura; Hiroyuki Shimanaka; Yoshitaka Wakebe; Tatsuo Kawamura; Eiichi Sugawara; Ken Okura; Masayuki Takahashi; Nobuo Takezawa, all of Tokyo (JP)

(73) Assignees: Dainichiseika Color & Chemicals Mfg. Co., Ltd.; Ukima Colour & Chemicals Mfg. Co., Ltd., both of Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/316,368

(22) Filed: May 21, 1999

Related U.S. Application Data

(63) Continuation of application No. 08/842,259, filed on Apr. 24, 1997, now Pat. No. 5,929,188.

(30) Foreign Application Priority Data

Apr. 30, 1996 (JP) .................................................. 8-130624

(51) Int. Cl.$^7$ ............................ C07C 267/00; C08K 5/29
(52) U.S. Cl. ...................... 525/131; 525/330.5; 525/424; 525/437; 525/440; 525/420; 525/453; 525/457; 525/523; 525/528; 427/385.5; 427/386; 427/388.2; 427/389.9; 427/391; 427/393; 427/393.5; 8/445; 8/465; 8/466; 528/68; 528/69; 528/85; 564/252

(58) Field of Search ..................................... 525/453, 457, 525/523, 528, 420, 424, 437, 440, 131, 330.5; 427/385.5, 386, 388.2, 389.9, 391, 393, 393.5; 8/445, 465, 466; 528/68, 69, 85; 564/252

(56) References Cited

U.S. PATENT DOCUMENTS 5,117,059   5/1992   Tylor .
5,136,006   8/1992   Sundararaman et al. .

*Primary Examiner*—Patricia A. Short
(74) *Attorney, Agent, or Firm*—Oblon, Spivak, McClelland, Maier & Neustadt, P.C.

(57) ABSTRACT

A polyfunctional polycarbodiimide compound contains at least four molecular chains bonded independently to a backbone. Each of the molecular chains contains a carbodiimido (—N═C═N—) group. The polyfunctional carbodiimide compound can be produced by reacting (a) an isocyanate compound having at least one carbodiimido group and at least one isocyanate group with (b) a polyol, polyamine and/or aminoalcohol having at least four hydroxyl, primary amino and/or secondary amino groups in a molecule. Also disclosed are a resin composition containing the polyfunctional polycarbodiimide compound as a crosslinking agent; and a treatment method of an article, which makes use of the resin composition.

8 Claims, No Drawings

POLYCARBODIIMIDE COMPOUND, PRODUCTION PROCESS THEREOF, RESIN COMPOSITION, AND TREATMENT METHOD OF ARTICLE

This application is a continuation of Ser. No. 08/842,259 filed Apr. 24, 1997 now U.S. Pat. No. 5,929,188.

BACKGROUND OF THE INVENTION a) Field of the Invention This invention relates to a novel polycarbodiimide compound, a production process thereof, a resin composition, and a treatment method of an article.

b) Description of the Related Art

A variety of resinous treatments have conventionally been used for the resin finishing or color finishing of fibrous articles such as threads, yarns, strands, woven fabrics, nonwoven fabrics, and paper sheets. Further, diverse resin compositions have also been used to coat, resin-finish, surface-coat or print metal articles such as iron articles and aluminum articles, synthetic resin articles such as polyethylene, polypropylene polyvinyl chloride, ABS, polyester and nylon articles, plastic films such as polyethylene, polypropylene, polyvinyl chloride and polyester films, and wooden articles.

For example, a resin-base pigmented printing paste for a woven fabric contains a colorant, a polymeric binder and a crosslinking agent for the polymeric binder. Conventional usable examples of the polymeric binder include acrylate, vinyl and diene polymers containing reactive groups. They may be used in the form of aqueous emulsion polymerization mixtures. As such crosslinking agent, compounds containing one or more methylol, alkylmethylol, epoxy, isocyanate or cyclic ethylene-imine groups have been used to date. Similar polymeric binders and crosslinking agents have also been used in paints for metal articles, synthetic resin articles and wooden articles as well as gravure printing inks for plastic films.

In the fields of woven fabrics, paints, printing inks and the like, however, it is required, depending on the application, to effect crosslinking at a low temperature to room temperature without heating a resin at a high temperature upon crosslinking the same. It is also required from the hygienic standpoint that a resin composition for use in such fields be sufficiently non-toxic and safe.

To meet such requirements, carbodiimide compounds are attracting interests as crosslinking agents for polymeric binders. Recently, compounds with plural carbodiimido groups contained therein have been found to be useful as crosslinking agents for polymeric binders and also to have high levels of non-toxicity and safety. For example, it has been proposed to use as a crosslinking agent for a polymeric binder a linear carbodiimide compound available by reacting a carbodiimido-containing diisocyanate compound, which is in turn obtainable by condensation of plural molecules of a corresponding diisocyanate compound, with a monoisocyanate compound, a monohydric alcohol compound or a dihydric alcohol compound.

These carbodiimide compounds are highly valued in non-toxicity and safety over the conventional crosslinking agents and, when crosslinking is conducted at high temperatures, give satisfactory results. They are however accompanied by a drawback that, when crosslinking is conducted at low temperatures to room temperature, they cannot bring about satisfactory results in the dry/wet fastness to rubbing, the fastness to laundering, and the like especially when applied to woven fabrics of synthetic fibers. When used in paints, coating formulations, printing inks and the like, they cannot bring about satisfactory results either insofar as crosslinking is conducted at low temperatures to room temperature.

SUMMARY OF THE INVENTION

As is appreciated from the foregoing, there is an outstanding demand for a crosslinking agent which can achieve sufficient crosslinking of polymeric binders at low temperatures to room temperature in various applications while fully meeting non-toxicity and safety requirements.

It is therefore a primary object of the present invention to provide a crosslinking agent which has no problem in toxicity and safety and can sufficiently crosslink various polymeric binders at low temperatures to room temperature.

In one aspect of the present invention, there is thus provided a polyfunctional polycarbodiimide compound comprising at least four molecular chains containing a carbodiimido (—N=C=N—) group and bonded independently to a backbone.

The polyfunctional polycarbodiimide compound according to the present invention has no problem in toxicity and safety and is useful as a crosslinking agent for sufficiently crosslinking various polymeric binders at low temperatures to room temperature.

In another aspect of the present invention, there is also provided a process for the production of a polyfunctional carbodiimide compound, which comprises reacting (a) an isocyanate compound having at least one carbodiimido group and at least one isocyanate group with (b) a polyol, polyamine and/or aminoalcohol having at least four hydroxyl, primary amino and/or secondary amino groups in a molecule.

In a further aspect of the present invention, there is also provided a resin composition comprising a polymeric binder and a crosslinking agent, wherein the crosslinking agent is the above-described polyfunctional polycarbodiimide compound, and the polymeric binder has groups reactive with the crosslinking agent.

In a still further aspect of the present invention, there is also provided a method for the treatment of an article, which comprises applying the above-described resin composition to the article by a method selected from the group consisting of coating, textile printing, impregnation and printing, and then drying the resin composition.

DETAILED DESCRIPTION OF THE INVENTION AND PREFERRED EMBODIMENTS

The present invention will hereinafter be described in further detailed based on certain preferred embodiments.

The polyfunctional polycarbodiimide compound according to the present invention is compound in which four or more carbodiimido-containing molecular chains are independently bonded to a backbone chain. It can be obtained by reacting the isocyanate compound having one or more carbodiimido group and one or more isocyanate groups [(hereinafter called the "side chain component (a)"] with the polyol, polyamine and/or aminoalcohol having four or more hydroxyl, primary amino and/or secondary amino groups in a molecule [hereinafter called the "backbone component (b)"] and, if necessary, further reacting the monohydric alcohol or monoamine containing one hydroxyl group, primary amino group or secondary amino group in a molecule [hereinafter called the "terminal component (c)"].

Illustrative of the above-described polyfunctional polycarbodiimide compound are:

(1) Products which are each available by reacting an isocyanate compound (component a-1), which contains one or more carbodiimido groups and one isocyanate group, with the backbone component (b) at an equi-equivalent ratio, namely, at a ratio of 1:1 in equivalent.

(2) Products which are each available by reacting one of two isocyanate groups of an isocyanate group (component a-2), which contains one or more carbodiimido groups and the two isocyanate groups, with the backbone component (b) and then reacting the terminal component (c) with unreacted isocyanate groups, which are still remaining in the reaction product, at an equi-equivalent ratio, namely, at a ratio of 1:1 in equivalent.

(3) Products which are each available by reacting first the component (a-1) and then the component (a-2) with the backbone component (b) and further reacting the terminal component (c) with unreacted isocyanate groups, which are still remaining in the reaction product.

In each of the above-described reactions, a polyol, polyamine and/or aminoalcohol containing two or three hydroxyl, primary amino and/or secondary amino groups in a molecule may be added to the reaction system so that the molecular chain of the resultant compound is extended further.

The component (a-1) employed in the above-described reaction is available in a manner known per se in the art, namely, by reacting a di- or polyisocyanate compound, for example, in the presence of a carbodiimidation catalyst such as 3-methyl-1-phenyl-3-phosphorene-1-oxide to couple two isocyanate groups into a carbodiimide group while maintaining one of terminal isocyanate groups, and then reacting the remaining isocyanate group with a terminal component or a monoisocyanate compound.

On the other hand, the component (a-2) is available by reacting a di- or polyisocyanate compound in the presence of a similar carbodiimidation catalyst to couple two isocyanate groups into a carbodiimide group while maintaining an isocyanate group at a terminal of the resulting molecule.

No particular limitation is imposed on the number of carbodiimide group(s) in a molecule of each of the components (a-1) and (a-2). The number of such carbodiimide groups can however be from about 1 to 20, preferably from about 2 to 10 or so because these components are used as raw materials for crosslinking agents according to the present invention.

Examples of the di- or polyisocyanate compound employed in the present invention include conventionally known aliphatic diisocyanates, alicyclic diisocyanates, and aromatic diisocyanates. Specific examples are hexamethylene diisocyanate, isophorone diisocyanate, hydrogenated diphenylmethane diisocyanate, toluylene diisocyanate, diphenylmethane diisocyanate, and tetramethylxylylene diisocyanate; and polyisocyanate compounds available by dimerizing or trimerizing them through biuret bonds or isocyanurate bonds.

Illustrative of the monoisocyanate compound employed in the present invention are conventionally known aliphatic monoisocyanates, alicyclic monoisocyanates, aromatic monoisocyanates, and $\alpha,\beta$-ethylenically-unsaturated isocyanates. Specific examples are hexyl isocyanate, phenyl isocyanate, toluene isocyanate, methacryloyl isocyanate, methacryloyloxyethyl isocyanate, and m-isopropenyl-$\alpha,\alpha'$-dimethylbenzyl isocyanate.

Further, the backbone component (b) forming the polycarbodiimide compound according to the present invention can be one or more polyols, polyamines or aminoalcohols, each of which contains four or more hydroxyl, amino and/or imino groups in a molecule and is selected from known aliphatic, alicyclic or aromatic polyols, polyamines or aminoalcohols; esters of aliphatic, alicyclic or aromatic polycarboxylic acids with polyhydric compounds, said esters containing plural hydroxyl groups; or epoxy resin hydrates. Specifically, the backbone component (b) can be, for example, one or more polyols, polyamines or aminoalcohols selected from polyglycerins such as diglycerin, tetraglycerin, hexaglycerin or decaglycerin; pentaerythritol, dipentaerythritol, sorbitan, sorbitol and the like, and their ethylene oxide adducts and propylene oxide adducts; polyethylene-imines; ethylene oxide adducts and propylene oxide adducts of amines such as ethylenediamine, propylenediamine, hexamethylenediamine, diethylenetriamine and polyethyleneimine; ethylene oxide adducts and propylene oxide adducts of phenolic novolak resins; polyols available by reactions between bisphenol A-epichlorohydrin addition polymers and water, polyols available by reactions between polyglycerin polyglycidyl ethers and water, and polyols available by reactions between sorbitan polyglycidyl ethers and water; or alcohols which are partial esterification products of the above polyhydric alcohols and still contain four or more hydroxyl groups.

The terminal component (c), which can be reacted further as needed, can be one or more monohydric alcohols or monoamines selected from aliphatic, alicyclic or aromatic monohydric alcohols or monoamines; or aliphatic, alicyclic or aromatic polyhydric alcohol monohydroxypolyethers or monohydroxypolyesters; and monohydric alcohols containing one or more anionic or cationic groups. Specifically, the terminal component (c) can be, for example, one or more monohydric alcohols or monoamines selected from aliphatic, alicyclic or aromatic monohydric alcohols having 1–18 carbon atoms; monohydric alcohols available by monoetherifying polyalkylene glycols having 2–4 carbon atoms with aliphatic, alicyclic or aromatic monohydric alcohols having 1–18 carbon atoms; monohydric alcohols available by monoesterifying polyalkylene glycols having 2–4 carbon atoms with aliphatic, alicyclic or aromatic monocarboxylic acids having 1–18 carbon atoms; aliphatic, alicyclic or aromatic monoamines having 1–18 carbon atoms; or aliphatic, alicyclic or aromatic monohydric alcohols containing one or more anionic groups such as sulfonic groups, sulfate ester groups or phosphate ester groups or one or more cationic groups such as tertiary amino groups, quaternary ammonium groups or pyridinium groups. Specific examples include the sodium and triethylamine salts of sulfonic acids such as hydroxymethanesulfonic acid, hydroxyethanesulfonic acid, hydroxypropanesulfonic acid, monoethoxy-monohydroxyethyl sulfosuccinate, taurine, N-methyl-taurine, sulfanilic acid and metanilic acid; and 2-hydroxyethyltrimethylammonium chloride.

The polycarbodiimide compound (A) of the present invention as obtained as described above has an average molecular weight of from about 1,000 to 30,000, preferably from about 2,000 to 20,000.

A description will next be made about the polymeric binder (B) crosslinked by the polycarbodiimide compound (A) of the present invention. The polymeric binder (B) crosslinked by the polycarbodiimide compound (A) is a polymer containing one or more carboxyl groups, hydroxyl groups, amino groups, thiol groups or the like as reactive groups. The content of these reactive groups may range from about 0.1 to 10 wt. %, preferably from 0.5 to 5 wt. % based on the polymeric binder although it varies depending on the kind of the reactive groups. These polymeric binders are conventionally-known polymeric binders employed in various adhesives, paints, coating formulations, printing inks, resin-base pigmented printing pastes, resinous processing agents for textile, and the like. Illustrative of the polymeric binder (B) are addition polymers such as polyacrylate esters, polyvinyl compounds and polydienes; addition condensation polymers such as polyurethanes, polyurethane ureas and epoxy resins; condensation polymers such as alkyd resins, polyesters and polyamides; and derivatives of natural substances, such as rosin-modified resins and cellulose derivatives.

Where the polymeric binder is an addition polymer, the polymeric binder can be obtained by using as a comonomer an active-hydrogen-containing monomer— which is selected from the monomer group consisting of unsaturated carboxylic acids such as acrylic acid, methacrylic acid, maleic acid, fumaric acid and itaconic acid, their hydroxyl ($C_2$–$C_4$)alkyl esters, polyoxy($C_2$–$C_4$)alkylene esters and glyceryl esters, allyl alcohol, allylamine, and the monoesters and monoamines of the above-described unsaturated dicarboxylic acids—and copolymerizing the thus-selected monomer with another monomer. Usable examples of the monomer copolymerizable with the above-selected monomer include vinyl compounds such as vinyl chloride, vinyl acetate and styrene; alkylenes such as ethylene, butadiene and isoprene; acrylate esters such as $C_{1-18}$ alkyl acrylates, cyclohexyl acrylate and benzyl acrylate; and methacrylate esters such as $C_{1-18}$ alkyl methacrylates, cyclohexyl methacrylate and benzyl methacrylate. They can be used either singly or in combination.

Where the polymeric binder is an addition condensation polymer or a condensation polymer, the polymeric binder can be produced by using, as at least a portion of a monomer upon production of the polymer, trimellitic anhydride, pyromellitic anhydride, a half ester of such an acid anhydride and a diol, dimethylolpropionic acid, dimethylolbutyric acid, dimethylolvaleric acid, lysine, arginine, aspartic acid, glutamic acid or the like. To improve the dispersibility of a pigment, the compatibility of an article, and the like, a non-reactive polymeric binder can also used in combination with the above-described polymeric binder to an extent not impairing physical properties of a coating film to be formed.

The resin composition according to the present invention is composed of the compound (A) and the polymeric binder (B). The compound (A) can be used as a crosslinking agent in a proportion of from about 0.5 to 50 parts by weight, preferably from 1.0 to 30 parts by weight, more preferably from 3 to 20 parts by weight per 100 parts by weight of the polymeric binder (B).

Where the resin composition according to the present invention is intended to effect coloring like a resin-base pigmented printing paste or a paint, one or more of conventionally-known pigments, dyes, colored polymer beads, microencapsulated pigments and the like are used in combination. Illustrative pigments include phthalocyanine pigments, azo pigments, azomethineazo pigments, azomethine pigments, anthraquinone pigments, perinone/perylene pigments, indigo/thioindigo pigments, dioxazine pigments, quinacridone pigments, isoindolinone/isoindoline pigments, carbon black pigment, titanium oxide pigment, iron oxide pigment, calcined spinnel pigment, and extender pigments. Where these pigments are used in the resin composition according to the present invention, it is preferred to use them as high-concentration color dispersions by finely dispersing them beforehand with a surfactant or water-soluble or solvent-soluble polymer dispersant which has conventionally been known as a dispersion aid.

Examples of the article to be treated by the resin composition according to the present invention include metal articles, synthetic resin articles, plastic films, wooden products, woven fabrics, nonwoven fabrics, and paper sheets. Described more specifically, they are small articles such as iron products and aluminum products, large articles such as automotive vehicle bodies, metal articles such as buildings, articles made of synthetic resins such as polyethylene, polypropylene, polyvinyl chloride, ABS, polyesters and nylon, plastic films such as polyethylene, polypropylene, polyvinyl chloride and polyester films, wooden products such as wood products, plywood products and wooden buildings, and fibrous articles such as threads, yarns, strands, woven fabrics, nonwoven fabrics and paper sheets.

To treat these articles with the resin composition of the present invention by subjecting them to coating, textile printing, impregnation, printing, building-up, compression bonding or adhesion, methods similar to those known to date can be used. Crosslinking treatment of the polymeric binder as post-treatment in the above-mentioned use can be conducted at a high temperature, for example, at 100° C. or higher, although it can also be conducted at a temperature of room temperature or lower. Articles for which crosslinking treatment temperatures of from room temperature to 100° C. are desired are fibrous products, plastic film products, wooden products, large components, large structures, buildings and the like.

The present invention will next be described more specifically by the following Examples, in which all designations of "part" or "parts" and "%" mean part or parts by weight and wt. %.

Example 1 (Synthesis of Crosslinking Agent No. 1)

Charged in a condensation reactor—which was fitted with a stirrer, a thermometer, a water measuring trap equipped with a coiled condenser, a nitrogen gas inlet tube and a dropping funnel—were 631.4 parts of a 30% toluene solution of polyhexamethylenecarbodiimide diisocyanate (PHMCDIDI, average number of carbodiimido groups in a molecule: about 2.8) which had been obtained by condensing 4 molecules of hexamethylene diisocyanate while using 3-methyl-1-phenyl-3-phosphorene-1-oxide as a carbodiimidation catalyst, followed by the addition of 1.3 parts of a 5% methyl ethyl ketone (MEK) solution of dibutyltin dilaurate (DBTDL). The resultant mixture was heated to 60° C., at which 468.5 parts of a 50% toluene solution of polyethylene glycol monomethyl ether (PEGMME, molecular weight: about 1,000) were added dropwise over 60 minutes for reaction. The reaction mixture was then gradually heated, and the reaction was continued at 100° C. for 3 hours. Then, 37.6 parts of a 50% toluene solution of decaglyceryl monolaurate (average number of hydroxyl groups in a molecule: about 11) were added dropwise at 100° C. over 60 minutes, and the reaction was continued for further 1 hour. The end of the reaction was determined by confirming a reduction in isocyanate groups and formation of urethane groups by infrared absorption spectroscopy.

Next, the toluene was distilled off at 115° C. for 2 hours, and the reaction system was depressurized further to distill off the toluene further. At 50° C., 1,770 parts of water were added, whereby an aqueous solution (solid content: 20%) of the thus-formed polycarbodiimide (PCDI) compound (hereinafter called "the crosslinking agent No. 1") was obtained. The above reactions were conducted so that the PCDI compound was provided with a structure having 11 carbodiimido(CDI)-containing side chains and contained about 30 CDI groups in total in a molecule.

Example 2 (Synthesis of Crosslinking Agent No. 2)

In a similar manner as in Example 1, 574.0 parts of a 30% toluene solution of PHMCDIDI were charged in a condensation reactor, followed by the addition of 0.9 part of a 5% MEK solution of DBTDL. Then, 233.6 parts of a 50% toluene solution of polypropylene glycol monobutyl ether (molecular weight: about 500) were added dropwise for reaction. Next, 35.0 parts of a 50% toluene solution of dipentaerythritol monolaurate (average number of hydroxyl groups in a molecule: about 5) were added dropwise for further reaction. Toluene was thereafter added, whereby a toluene solution of the resulting PCDI compound (solid content: 20%) was obtained (hereinafter called "the crosslinking agent No. 2"). The above reactions were conducted so that the PCDI compound was provided with a structure having 5 carbodiimido(CDI)-containing side chains and contained about 14 CDI groups in total in a molecule.

Example 3 (Synthesis of Crosslinking Agent No. 3)

In a similar manner as in Example 1, 574.0 parts of a 30% toluene solution of PHMCDIDI were charged in a condensation reactor, followed by the addition of 0.9 part of a 5% MEK solution of DBTDL. Then, 233.6 parts of a 50% toluene solution of polyoxypropylenepolyoxyethylene (50:50) random copolymer monobutyl ether (molecular weight: about 500) were added dropwise for reaction. Next, 50.4 parts of a 50% toluene solution of polyoxyethylene (6) sorbitol monolaurate (POE6SML, average number of hydroxyl groups in a molecule: about 5) were added dropwise for further reaction. Toluene was thereafter added, whereby a toluene solution of the resulting PCDI compound (solid content: 20%) was obtained (hereinafter called "the crosslinking agent No. 3"). The above reactions were conducted so that the PCDI compound was provided with a structure having 5 carbodiimido(CDI)-containing side chains and contained about 14 CDI groups in total in a molecule.

Example 4 (Synthesis of Crosslinking Agent No. 4)

In a similar manner as in Example 1, 574.0 parts of a 30% propylene glycol monomethyl acetate (hereinafter called "PGMEA") solution of PHMCDIDI were charged in a condensation reactor, followed by the addition of 0.9 part of a 5% MEK solution of DBTDL. Then, 31.0 parts of a 50% PGMEA solution of PEGMME (molecular weight: about 550) were added dropwise for reaction. Next, 50.4 parts of a 50% PGMEA solution of POE6SML were added dropwise for further reaction. After cooling, PGMEA was added to give a solid content of 20%, whereby a PGMEA solution of the resulting PCDI compound (solid content: 20%) was obtained (hereinafter called "the crosslinking agent No. 4"). The above reactions were conducted so that the PCDI compound was provided with a structure having 5 carbodiimido(CDI)-containing side chains and contained about 14 CDI groups in total in a molecule.

Example 5 (Synthesis of Crosslinking Agent No. 5)

In a similar manner as in Example 1, 376.4 parts of a 30% PGMEA solution of polytoluylenecarbodiimide diisocyanate (PTCDIDI) were charged in a condensation reactor, followed by the addition of 0.9 part of a 5% MEK solution of DBTDL. Then, 231.0 parts of a 50% PGMEA solution of PEGMME (molecular weight: about 550) were added dropwise for reaction. Next, 50.4 parts of a 50% PGMEA solution of POE6SML were added dropwise for further reaction. After cooling, PGMEA was added to give a solid content of 20%, whereby a PGMEA solution of the resulting PCDI compound (solid content: 20%) was obtained (hereinafter called "the crosslinking agent No. 5"). The above reactions were conducted so that the PCDI compound was provided with a structure having 5 carbodiimido(CDI)-containing side chains and contained about 14 CDI groups in total in a molecule.

Example 6 (Synthesis of Crosslinking Agent No. 6)

In a similar manner as in Example 1, 376.4 parts of a 30% mineral terpin solution of PTCDIDI were charged in a condensation reactor, followed by the addition of 0.7 part of a 5% MEK solution of DBTDL. Then, 61.1 parts of a 50% mineral terpin solution of oleyl alcohol were added dropwise for reaction. Next, 50.4 parts of a 50% mineral terpin solution of POE6SML were added dropwise for further reaction. After cooling, mineral terpin was added to give a solid content of 20%, whereby a mineral terpin solution of the resulting PCDI compound (solid content: 20%) was obtained (hereinafter called "the crosslinking agent No. 6"). The above reactions were conducted so that the PCDI compound was provided with a structure having 5 carbodiimido(CDI)-containing side chains and contained about 14 CDI groups in total in a molecule.

Example 7 (Synthesis of Crosslinking Agent No. 7)

In a similar manner as in Example 1, 376.4 parts of a 30% toluene solution of PTCDIDI were charged in a condensation reactor, followed by the addition of 0.6 part of a 5% MEK solution of DBTDL. Then, 34.2 parts of a 50% toluene solution of n-butanol were added dropwise for reaction. Next, 50.4 parts of a 50% toluene solution of POE6SML were added dropwise for further reaction. After cooling, toluene was added to give a solid content of 20%, whereby a toluene solution of the resulting PCDI compound (solid content: 20%) was obtained (hereinafter called "the crosslinking agent No. 7"). The above reactions were conducted so that the PCDI compound was provided with a structure having 5 carbodiimido(CDI)-containing side chains and contained about 14 CDI groups in total in a molecule.

Example 8 (Synthesis of Crosslinking Agent No. 8)

In a similar manner as in Example 1, 376.4 parts of a 30% PGMEA solution of PTCDIDI were charged in a condensation reactor, followed by the addition of 0.9 part of a 5% MEK solution of DBTDL. Then, 32.9 parts of a 50% PGMEA solution of sulfanyltriethylamide and 22.2 parts of a 50% PGMEA solution of n-butanol were added dropwise for reaction. Next, 50.4 parts of a 50% PGMEA solution of POE6SML were added dropwise for further reaction. After cooling, PGMEA was added to give a solid content of 20%, whereby an aqueous solution of the resulting PCDI compound (solid content: 20%) was obtained (hereinafter called "the crosslinking agent No. 8"). The above reactions were conducted so that the PCDI compound was provided with a structure having 5 carbodiimido(CDI)-containing side chains and contained about 14 CDI groups in total in a molecule.

Use Example 1 (Textile-Printing of Woven Fabric)

Mixed into a solution were 20 parts of an ethyl acrylate-styrene-acrylic acid (60:36:4) copolymer latex (solid content: 40%), 5 parts of the crosslinking agent No. 1 (solid content: 20%), 10 parts of water and 5 parts of an aqueous polyoxyethylene alkylphenyl ether (solid content: 20%). While stirring the resultant solution in a homomixer, 55 parts of mineral terpin were gradually added to form an o/w emulsion. Five parts of an aqueous dispersion of copper phthalocyanine blue pigment were added, and the resulting mixture was thoroughly mixed so that a blue-pigmented resin-base printing paste was prepared.

A knitted cotton fabric was printed with the blue-pigmented resin-base printing paste by a screen printing machine and was then dried at room temperature, thereby obtaining a printed fabric which was excellent in various fastnesses such as dry/wet fastness to rubbing, fastness to laundering and dry-cleaning resistance, was soft and was of a blue color developed vividly. In addition, textile printing pastes were also prepared using the crosslinking agents Nos. 4, 5 and 6, respectively, instead of the crosslinking agent No. 1, and printing was conducted in a similar manner as described above. Printed fabrics excellent in various fastnesses, soft and vivid in the developed color were obtained.

Use Example 2 (Waterproofing Water-Repellant Finishing of Woven Fabric)

Added to 90 parts of an ethyl acetate solution of a butyl acrylate-acrylic acid (95:5) copolymer (acrylic rubber) (solid content: 20%) and 5 parts of the crosslinking agent No. 2 (solid content: 20%) were 10 parts of a green solution (pigment content: 10%, resin content: 10%) which had been obtained by dispersing copper phthalocyanine green pigment in an ethyl acetate solution of a butyl acrylate-acrylic acid copolymer. The resultant mixture was thoroughly mixed so that a green coating formulation was prepared.

A tufted polyester fabric was coated with the green coating formulation by a coating machine to give a resin coat weight (wet weight) of 30 g/m$^2$. The thus-coated fabric was provisionally dried at 50° C. for 5 minutes and was then baked at 130° C. for 3 minutes. The fabric was then subjected to padding through a toluene solution of a fluorinated silicone resin, whereby its waterproofing water-repellant finishing was conducted. A coated fabric excellent in moisture impermeability, water pressure resistance, dry/wet fastness to rubbing and fastness to laundering and having a superb green color was obtained. In addition, coating formulations were also prepared using the crosslinking agents Nos. 4, 5, 6 and 7, respectively, instead of the crosslinking agent No. 2, and coating and waterproofing water-repellant finishing were conducted in a similar manner as described above. Coated fabrics excellent in various fastnesses were obtained.

Use Example 3 (Moisture Permeable Coating Treatment of Woven Fabric)

Polytetramethylene glycol (average molecular weight: 1,000), ethylene glycol and dimethylolpropionic acid (glycol components), and diphenylmethane diisocyanate (diisocyanate component) were reacted at a molar ratio of 0.4:0.3:0.3:1.0 in MEK, whereby a milky white polyurethane dispersion (solid content: 30%) was obtained.

On the other hand, a polyoxypropylene-polyoxyethylene block copolymer (70/30) (glycol component) and diphenylmethane diisocyanate (diisocyanate component) were reacted at a molar ratio of 1:1 in MEK, whereby a polyurethane solution (solid content: 50%) was obtained.

Thoroughly mixed were 100 parts of the polyurethane dispersion obtained above, 5 parts of the polyurethane solution also obtained above, and 2 parts of the crosslinking agent No. 3. Under stirring in a homomixer, 120 parts of an MEK-toluene-water mixed solvent (weight ratio: 1:1:4) were added. The resultant mixture was stirred into an intimate mixture, whereby a w/o polyurethane emulsion (solid content: 14%) was prepared.

A woven polyester fabric was coated at a surface thereof with the above-obtained w/o polyurethane emulsion to give a coat weight of about 200 g/m$^2$. The thus-coated fabric was then dried at 80° C. for 3 minutes to form a porous layer. The thus-finished textile product had excellent water vapor transmission and, despite the porous layer, showed excellent dry/wet fastness to rubbing. In addition, w/o polyurethane emulsions were also prepared using the crosslinking agents Nos. 4, 5, 6, 7 and 8, respectively, instead of the crosslinking agent No. 3 and coating and drying were conducted in a similar manner as described above. Finished textile products having excellent water vapor transmission and dry/wet fastness to rubbing were obtained.

Use Example 4 (Water-Based Adhesive)

A water-based adhesive was prepared by adding 5 parts of the crosslinking agent No. 1 (solid content: 20%) to 100 parts of an aqueous dispersion (solid content: 40%) of a triethylamine-neutralized product of an anionic urethane urea resin which was a reaction product of polytetramethylene glycol (average molecular weight: about 1,000), dimethylolpropionic acid, isophorone diisocyanate and diethylenetriamine (weight ratio: 247:24:124:5).

A polypropylene (OPP) film, which had a thickness of 20 μm, had been subjected to corona discharge treatment and had a wetting index of 40 dyn/cm, was coated with the above water-based adhesive to give a solid coat thickness of 2.5 μm. Immediately after drying, a polypropylene (CPP) film having a wetting index of 38 dyn/cm and a thickness of 60 μm was dry-laminated at about 60° C. through laminating rolls. After the resultant laminated film was aged at 40° C. for 48 hours, a specimen of 15 mm in width was prepared. Using a Schopper tensile tester, its adhesion strength was measured at a pulling speed of 100 mm/min and 25–26° C. The specimen showed 173 g/15 mm as its adhesion strength.

For the sake of comparison, a laminated film was produced in a similar manner as described above except that in place of decaglyceryl monolaurate employed above in the preparation of the crosslinking agent No. 1, a linear crosslinking agent prepared using diethylene glycol in an equivalent amount was used. Its adhesion strength as measured likewise. The adhesion strength was found to be 110 g/15 mm.

From the above-described results, the adhesive making use of the crosslinking agent according to the present invention was found to have superior adhesive properties to the adhesive making use of the linear crosslinking agent. In addition, water-based adhesives were also prepared in a similar manner as described above except for the use of the crosslinking agents Nos. 4, 5 and 8, respectively, instead of the above-described crosslinking agent No. 1, and coating and lamination were conducted in a similar manner as described above. Laminated films having excellent adhesive properties were obtained.

Use Example 5 (Water-Based Adhesive)

A water-based adhesive was prepared by adding 5 parts of the crosslinking agent No. 1 (solid content: 20%) to 100 parts of an aqueous dispersion (solid content: 40%) of a triethylamine-neutralized product of an anionic urethane resin which was a reaction product of polycaprolactonediol (average molecular weight: about 2,000), 1,6-hexanediol, dimethylolpropionic acid and toluylene diisocyanate (weight ratio: 225:13:12:87).

In a similar manner as in Use Example 4, an OPP film was coated with the water-based adhesive and dried followed by the lamination of a CPP film. The adhesion strength of the laminated film was measured. It showed 151 g/15 mm as its adhesion strength. The adhesion strength of a laminated film obtained by using the linear non-branched crosslinking agent employed in Use Example 4 instead of the crosslinking agent No. 1 for the sake of comparison was 90 g/15 mm. The adhesive making use of the crosslinking agent according to the present invention therefore also showed superior adhesive properties to the adhesive making use of the linear crosslinking agent. In addition, water-based adhesives were also prepared by using the crosslinking agents Nos. 4, 5 and 8, respectively, instead of the above-described crosslinking agent No. 1, and coating and lamination were conducted in a similar manner as described above. Laminated films having excellent adhesive properties were obtained.

Use Example 6 (Water-Based Gravure Ink)

A mixture—which consisted of 40 parts of titanium oxide white pigment, 10 parts of a styrene-monobutyl maleate (molar ratio: 40:60) copolymer (average molecular weight: about 3,500), 10 parts of isopropyl alcohol, 38.5 parts of water, 1 part of a pigment dispersant and 0.5 part of a silicone antifoaming agent—was kneaded and dispersed twice in a sand mill, whereby a white pigment base color was prepared.

Added to 50 parts of the white pigment base color were 40 parts of the aqueous anionic urethane urea resin dispersion (solid content: 30%) used in Use Example 4, 0.5 part of fine powdery silicic anhydride, 0.5 part of polyethylene wax, 0.1 part of a silicone antifoaming agent and 8.9 pats of water. The resultant mixture was mixed in a sandmill into an intimate mixture, followed by the addition of 1 part of the crosslinking agent No. 1. The resultant mixture was mixed and its pH was adjusted to 8 with aqueous ammonia, whereby a white printing ink was obtained.

A nylon film of 20 $\mu$m in thickness was subjected to corona discharge treatment and was then coated with the above-obtained white printing ink by a No. 4 bar coater. The thus-coated film was dried and then aged at 40° C. for 48 hours. Using a cellophane adhesive tape, an adhesion strength test of the printed ink layer was conducted. As a result, the printed ink layer was found to have good adhesive properties.

To form a bag-making laminated film, a dry-lamination adhesive which was added with 10 parts of a carboxyl-containing polyester adhesive (ethyl acetate solution, solid content: 63%) and 3.8 parts of the crosslinking agent No. 7 was provided. The above nylon film was coated, on the side printed in a white color, with the dry-lamination adhesive to give a solid coat thickness of 3 $\mu$m was given. A polypropylene film of 60 $\mu$m in thickness, which had been subjected to corona discharge treatment, was laminated immediately. The laminated film was aged at 40° C. for 48 hours, and was then formed into a bag. The bag of the laminated film was filled with tap water and was then subjected to a boiling test at about 90° C. for 30 minutes. As a result, the external appearance of the surface of the bag was found to remain good without substantial pinhole-like separation.

For the sake of comparison, a white printing ink was also prepared in a similar manner as described above by using the linear crosslinking agent, which had been used for the sake of comparison in Use Example 4, instead of the crosslinking agent No. 1. A nylon film was printed with the white printing ink, followed by the lamination of a polypropylene film. In an adhesion strength test of the printed ink layer in which a cellophane adhesive tape was used, good results were shown in adhesive properties. However, as a result of a boiling test of a bag made from the laminated film and filled with tap water, marked pinhole-like separation was observed, and substantial wrinkles were observed on the surface.

From the foregoing results, the adhesive making use of the crosslinking agent according to the present invention demonstrated to have superior adhesive properties to the adhesive making use of the linear crosslinking agent. In addition, white printing inks were also prepared by using the crosslinking agents Nos. 4 and 5, respectively, instead of the above-described crosslinking agent No. 1. In a similar manner, nylon films were printed, followed by the lamination of polypropylene films, respectively. Laminated films having excellent adhesive properties and boil-proofness were obtained.

Use Example 7 (Water-Based Gravure Ink)

A water-based white gravure ink was prepared by mixing 35 parts of titanium oxide white pigment, 50 parts of an aqueous solution (solid content: 50%) of a carboxyl-containing polyurethane resin obtained from a carbonate polyol and an aliphatic isocyanate, 5 parts of an aqueous wax dispersion (solid content: 30%), 1 part of an antifoaming agent, 9 parts of water and 5 parts of the crosslinking agent No. 1. On the side, a water-based blue gravure ink as also prepared by mixing 15 parts of phthalocyanine blue pigment, 60 parts of an aqueous solution of a carboxyl-containing polyurethane resin, 5 parts of an aqueous wax dispersion, 1 part of an antifoaming agent, 19 parts of water and 5 parts of the crosslinking agent No. 1.

Using the water-based, blue and white gravure inks obtained above, plastic films such as polyethylene, polypropylene, polyester and nylons films were gravure-printed. Among the printed films so obtained, the printed films for use in lamination were able to withstand boiling and retorting treatment and those subjected to surface printing were excellent in heat resistance and chemical resistance.

Printed films were also obtained using water-based gravure inks which made use of an aqueous solution of a known carboxyl-containing acrylic resin and an aqueous solution of a known carboxyl-containing polyester resin, respectively, instead of the aqueous solution of the carboxyl-containing polyurethane resin employed above. Among the printed films so obtained, the printed films for use in lamination were also able to withstand boiling and retorting treatment and those subjected to surface printing were also excellent in heat resistance and chemical resistance.

Further, gravure inks were also prepared using the crosslinking agents Nos. 4 and 5, respectively, in place of the above-described crosslinking agent No. 1. Plastic films were gravure-printed likewise, whereby printed films for use in lamination, said printed films being withstandable through boiling and retorting treatment, and surface-printed films having excellent heat resistance and chemical resistance were obtained.

Use Example 8 (Woodgraining Gravure Ink)

Twelve parts of a vinyl chloride-vinyl acetate-acrylic acid (molar ratio: 89:6.7:4.3) copolymer (average molecular weight: about 30,000) were dissolved in 71 parts of a butyl acetate-methyl isobutyl ketone-xylene (weight ratio: 43:20:20) mixed solvent, followed by the addition of 2 parts of carbon black pigment. The resultant mixture was charged in a ball mill and was then dispersed for 16 hours. Further, 3 parts of silica were added and mixed, followed by the addition of 12 parts of the crosslinking agent No. 2. The thus-obtained mixture was mixed, whereby a black gravure ink was obtained. On the side, a woodgrain pattern was printed by a printing process on a surface of a semirigid polyvinyl chloride film which was colored in a light brown color to imitate a woodgrain. A translucent, semirigid polyvinyl chloride film was laminated under heat on the surface and at the same time, grooves in the form of a growth ring pattern were formed by embossing. Those grooves had an average depth in a range of from about 60 to 70 μm.

While allowing the above-obtained black gravure ink to flow downwards, the entire surface was coated by a knife coater so that the above-formed grooves were filled with the black ink and a fog-like thin ink layer of about 1 μm or less was formed over the entire film.

Further, the surface was coated through a gravure solid form plate with a topcoating formulation which was composed of an acrylic resin containing carboxyl groups and hydroxyl groups and the above-employed crosslinking agent No. 2, whereby a topcoat layer of about 60 to 70 μm was formed. As a consequence, a polyvinyl chloride sheet printed with the woodgrain and containing the growth ring pattern was obtained. Drying of the colored ink and the topcoat formulation was conducted at room temperature, followed by aging for 3 days in a constant-temperature chamber of 30 to 40° C.

The thus-obtained sheet was free from shrinkage, and the grooves remained unchanged. It was an attractive woodgrained sheet with the clear pattern. Further, the growth ring pattern showed excellent solvent resistance in a solvent resistance test in which thinner was used. In addition, gravure inks and topcoat formulations were also prepared using the crosslinking agents Nos. 3, 4, 5, 6 and 7, respectively, in place of the above-described crosslinking agent No. 2. They were coated likewise, whereby woodgrained sheets having a clear pattern and superb solvent resistance were obtained.

Use Example 9 (Painting of Wooden Products)

An outdoor white emulsion paint was prepared in accordance with the following formula: 33 parts of a methyl methacrylate-ethyl acrylate-acrylic acid (molar ratio: 64:32:4) copolymer latex (solid content: 40%), 22 parts of titanium oxide white pigment, 3 parts of mica, 7 parts of talc, 10 parts of a 3% aqueous hydroxyethylcellulose solution, 1 part of a pigment dispersant, 1 part of propylene glycol monomethyl ether, 2 parts of ethylene glycol, 0.5 part of a silicone antifoaming agent, 0.5 part of a preservative, 5 parts of the crosslinking agent No. 1 (solid content: 20%) and 15 parts of water. With this paint, exteriors of various buildings were painted in a white color. Paint films were allowed to undergo crosslinking at environment temperature, whereby painting excellent in physical properties such as weatherability, durability and waterproofness was successfully achieved. In addition, emulsion paints were also prepared using the crosslinking agents Nos. 4, 5 and 8, respectively, instead of the above-described crosslinking agent No. 1. With these emulsion paints, it was also possible to perform painting excellent in physical properties in a similar manner as described above.

Use Example 10 (Painting of Metal Products)

A gray acrylic paint for metal products was prepared in accordance with the following formula: 17.9 parts of titanium oxide white pigment, 0.2 part of carbon black, 0.6 part of iron oxide red pigment, 46.8 parts of an ethyl acetate solution (solid content: 60%) of a methyl methacrylate-ethyl methacrylate-octyl methacrylate-hydroxyethyl methacrylate-methacrylic acid (molar ratio: 45:20:20:10:5) copolymer, 14 parts of the crosslinking agent No. 2 (solid content: 20%), 0.1 part of a flooding preventive and 20.4 parts of xylol. Using this paint, various metal products of machines and office equipments were painted in a gray color. As a paint dryable at environment temperature or crosslinkable by baking at low temperatures, the above-prepared paint was able to perform painting excellent in physical properties such as weatherability, durability and waterproofness. In addition, paints for metal products were also prepared using the crosslinking agents Nos. 4, 5, 6 and 7, respectively, instead of the above-described crosslinking agent No. 2. With these paints, it was also possible to perform painting excellent in physical properties in a similar manner as described above.

Use Example 11 (coating Formulation for Polyvinyl Chloride Flooring Materials)

A water-based coating formulation for flooring materials was prepared by mixing 95 parts of an aqueous solution (solid content: 30%) of a carboxyl-containing polyurethane resin obtained from a polycarbonate polyol and an aliphatic isocyanate, 5 parts of silica, 0.5 part of a leveling agent, 0.1 part of an antifoaming agent and 3 parts of the crosslinking agent No. 1. Using a No. 10 bar coater, an elongated polyvinyl chloride flooring material was coated with the coating formulation to a thickness of about 5 μm, followed by drying at 100° C. for 1 minute. To determine effects of the crosslinking agent, specimens were obtained. An antiblocking test (30 minutes after drying; 2 kg/cm² load, 60° C., 48 hours), an alcohol resistance test (upon an elapsed time of 24 hours after drying; room temperature, 24 hour anti-spot test) and an MEK resistance test (upon an elapsed time of 24 hours after drying; 1 kg/cm² load, 20-stroke rubbing test) were conducted. As a result, the specimens were found to be superior in all the tests to those obtained without using any crosslinking agent. Especially in the antiblocking test, the specimen obtained without using any crosslinking agent was considerably inferior and showed a substantial difference. In addition, coating formulations for flooring materials were also prepared using the crosslinking agents Nos. 4, 5 and 8, respectively, instead of the above-described crosslinking agent No. 1. With these coating formulations, it was also possible to perform coating excellent in physical properties in a similar manner as described above.

Example 12 (Coating Formulation for Polypropylene Bumper Moldings)

A water-based bumper coating formulation was prepared by mixing 50 parts of an aqueous solution (solid content: 40%) of a carboxyl-containing polyurethane resin obtained from a carbonate polyol and an aliphatic isocyanate, 10 parts of talc, 20 parts of calcium carbonate, 5 parts of N-methyl-2-pyrrolidone, 1 part of a 5% aqueous solution of hydroxyethylcellulose, 0.5 part of a leveling agent, 30 parts of a water-base titanium oxide pigment base color (pigment content: 65%), 1 part of a water-base quinacridone red pigment base color (pigment content: 25%), 100 parts of water and 2.2 parts of the crosslinking agent No. 1. A polypropylene molding for a bumper, which had been subjected at a surface thereof to corona discharge treatment, was coated with the coating formulation by a spray gun to give a dry coat thickness of about 30 to 40 μm. The thus-coated molding was dried for 15 minutes by hot air of 50° C., whereby a coating film excellent in adhesion and durability was obtained. In addition, water-based coating formulations were also prepared using the crosslinking agents Nos. 4, 5 and 8, respectively, instead of the above-described crosslinking agent No. 1. With these coating formulations, it was also possible to perform coating excellent in physical properties in a similar manner as described above.

What is claimed is:

1. A polyfunctional polycarbodiimide compound comprising at least four molecular chains containing a carbodiimido (—N=C=N—) group and bonded independently to a backbone;

which is a reaction product of an isocyanate compound having at least one carbodiimido group and at least one isocyanate group and (b) a polyol, polyamine and/or aminoalcohol having at least four hydroxyl, primary amino and/or secondary amino groups in a molecule; and with (c) a monohydric alcohol or monoamine having one hydroxyl, primary amino or secondary amino group in a molecule, said polyfunctional polycarbodiimide compound having a molecular weight of from 1,000 to 30,000.

2. A resin composition comprising a polymeric binder and a crosslinking agent, wherein said crosslinking agent is the polyfunctional polycarbodiimide compound of claim, and said polymeric binder has groups reactive with said crosslinking agent.

3. The resin composition of claim 2, wherein said groups of said polymeric binder are selected from the group consisting of carboxyl, hydroxyl and amino groups.

4. The resin composition of claim 2, which is an adhesive, a coating formulation, a resinous processing agent for textile, a paint, a printing ink or a resin-base pigmented printing paste.

5. The resin composition of claim 2, further comprising a colorant.

6. A method for the treatment of an article, which comprises applying the resin composition of claim 2 to said article by a method selected from the group consisting of coating, textile printing, impregnation and printing, and then drying said resin composition.

7. The method of claim 6, wherein said resin composition further comprises at least one of pigments, dyes, antifoaming agents, thickeners and leveling agents.

8. The method of claim 6, wherein said article is selected from the group consisting of metal articles, synthetic resin articles, plastic films, wooden products, threads, yarns, strands, woven fabrics, nonwoven fabrics and paper sheets.

* * * * *